United States Patent
Knapp et al.

(10) Patent No.: US 7,217,417 B2
(45) Date of Patent: May 15, 2007

(54) GEL-BASED COSMETIC AND WOUND-HEALING FORMULATION AND METHOD

(75) Inventors: Barry Knapp, Irvine, CA (US); Ronald DiSalvo, Marina Del Rey, CA (US)

(73) Assignee: Dermacia, Inc., Newport Beach, CA (US)

( * ) Notice: Subject to any disclaimer, the term of this patent is extended or adjusted under 35 U.S.C. 154(b) by 107 days.

(21) Appl. No.: 10/440,990

(22) Filed: May 19, 2003

(65) Prior Publication Data

US 2004/0101515 A1 May 27, 2004

(51) Int. Cl.
*A61Q 5/12* (2006.01)
*A61K 31/74* (2006.01)
*A61K 36/06* (2006.01)
*A01N 63/00* (2006.01)

(52) U.S. Cl. .............................. 424/195.16; 424/93.51; 424/70.12; 424/78.03; 514/944; 514/844

(58) Field of Classification Search ........... 424/195.16, 424/70.12, 78.03, 93.51; 514/944, 844
See application file for complete search history.

(56) References Cited

U.S. PATENT DOCUMENTS 5,776,494 A * 7/1998 Guskey et al.
6,060,072 A * 5/2000 Konik et al.
6,303,105 B1 * 10/2001 Shah et al.

FOREIGN PATENT DOCUMENTS

GB 2031441 A * 4/1980

OTHER PUBLICATIONS

Web page from www.cabot-corp.com, with header of Cabot Glossary Term , printed Oct. 24, 2005.
Properites of CAB-O-SIL® M-5P Fumed Silica, www.cabot-corp.com , 2004.

* cited by examiner

*Primary Examiner*—Michele Flood

(57) ABSTRACT

Disclosed are gel-based cosmetic and wound-healing formulations, methods for making said formulations, and a method for simultaneously treating and concealing injuries to human skin. In one exemplary embodiment, the cosmetic and wound-healing formulation comprises live yeast cell extract, pigment, and a gel.

6 Claims, No Drawings

GEL-BASED COSMETIC AND WOUND-HEALING FORMULATION AND METHOD

BACKGROUND OF THE INVENTION

1. Field of the Invention

The present invention relates to compositions applied to the skin for cosmetic and healing purposes.

2. Description of the Related Art

Both cosmetic creams and healing creams are well known. Both of these types of topically applied compositions are frequently made with a petroleum base to deliver pigments and healing factors to the skin.

Cosmetic creams typically include a hydrocarbon base in combination with pigments. Occlusive natural oils and synthetic long-chain hydrocarbons have been used in construction of modern makeup or foundation bases. Such oils and hydrocarbons impart sheen, function as binders for the waxy components in the formula, and form the bases of the oil phase of conventional emulsion systems.

Physicians often prescribe to patients wound-healing creams to expedite healing of wounds and the surrounding skin. Live yeast cell extract (LYCE), Aloe Vera, colostrum and Vitamin E are examples of common healing factors. LYCE, which has been variously called Biodynes, Skin Respiratory Factors, and Tissue Respiratory Factors, can be harvested from the nucleus of *saccharmoyces cerevisiae* cells after the yeast has been cultured in an appropriate nutritional media and then stressed by heat, or by UV radiation (~286 nm), x-rays or chemical injury. Irradiation and especially elevated temperatures produce heat stress, or heat-shock proteins, in all cells (Demple, B. 1998. Signal transduction: a bridge to control. *Science* 279(5357) 1655). Elevated temperature causes cellular proteins to lose their three-dimensional structure, and heat stress proteins are capable of restoring the original configuration. If the cell is then removed and its protoplasm concentrated, LYCE may be obtained. LYCE can be prepared as an alcohol extract of viable *Saccharomyces Lysate*. LYCE stimulates wound oxygen consumption, epitheliazation, and collagen synthesis. In topical medicinal preparations, LYCE is characterized and quantified in terms of Skin Respiratory Factor (SRF) units. A unit of activity is calculated as the amount of SRF which is required to increase the oxygen uptake of 1 mg of dry weight rat abdominal skin by 1 percent at the end of a 1 hour testing period in a Warburg apparatus.

LYCE-biofactors harvested from *saccharmoyces cerevisiae* contain nutrients such as peptides, proteins, amino acids, minerals carbohydrates, nucleic acid and other gene products. After processing, LYCE-biofactors are clear and sediment-free, retaining the active components without the dark color or odor of the starting material (Fishman, H. M. 2001. Yeast Has Applications In The Cosmetics Industry, *HAPPI*, July, 42). LYCE biofactors may induce a respiratory response in viable cells, as measured by Warburg Assay, by spectrophotometric absorbance, or by oxygen electrode measurement of cultured human fibroblasts (Lods, L., D. Scholz, C. Dres, C. Johnson & G. Brooks. 2000. Peroxide-Inducible Protective Factors Produced by *Saccharomyces cerevisiae. Cosmet & Toil* 115(12) 61-6. Fishman, H. M. 2001. Yeast Has Applications In The Cosmetics Industry, *HAPPI*, July, 42). Further, when delivered to the lower strata of the skin, LYCE biofactors stimulate oxygen consumption by viable cells, causing cellular proliferation and collagen and elastin synthesis.

Temporary cosmetic side effects, such as swelling, bruising, or visible scars, commonly result from plastic surgery or other injuries to skin. It may take days, weeks, or even months before wounds heal and such side effects disappear. Historically, healing creams and cosmetic creams have been used independently to heal and disguise skin wounds.

SUMMARY OF THE INVENTION

The present invention relates to a gel-based formulation containing pigments and wound-healing agents, which simultaneously aids in healing skin wounds and concealing damage to the skin.

One aspect of the invention includes a gel-based formulation, including: live yeast cell extract, isododecane, silicon-containing compounds, and metal-based pigment. In one preferred embodiment of the formulation, the live yeast cell extract and pigment are suspended in the gel. The pigments in the formulation are preferably titanium dioxide and iron oxide. Silica, silicone-grafted copolymers, and silicone gelling agents are the preferred silicone-containing compounds in the formulation. The gel preferably contains a combination of ethylene, butylene, propylene, and styrene.

Another aspect of the invention includes a method of topically applying a gel-based formulation to simultaneously heal and disguise wounds on human skin.

Another aspect of the invention includes a method of preparing a formulation for topical application. One preferred method involves homogenizing a gel in a cold process and assimilating a live yeast cell extract and a pigment into the gel during the homogenizing of the gel. The isododecane may be pre-mixed with ethylene, propylene, styrene, and butylene in a homogenizer. Another preferred embodiment involves creating a gel using a roller mill and assimilating a live yeast cell extract and a pigment into the gel during the creation of the gel.

DETAILED DESCRIPTION OF THE PREFERRED EMBODIMENT

One embodiment of the present invention comprises a gel-based formulation that can be applied topically to the skin. Pigments and LYCE can be suspended within the gel-based formulation. The LYCE can be present in an aqueous state and surrounded by two or more membrane layers of pigmented gel. In one preferred embodiment, the gel contains isododecane, silicon-containing compounds, ethylene/propylene/styrene and ethylene/butylene/styrene based copolymers. Gel, as opposed to petroleum, facilitates oxygenation of the skin and does not clog pores in skin. Thus, the gel-based formulation is particularly well-suited for use on open wounds. For example, the formulation can be used to promote healing and to conceal swelling, bruising, or visible scars associated with wounds. The formulation is particularly well-suited for use during the recovery phase following a surgical procedure.

In one preferred embodiment, isododecane serves as the primary non-water liquid and solvent for the formation of a unique gel base which, in combination with other moieties, forms a linear polymer meshwork. Isododecane may be combined with other heavier emollients to give a balanced, relatively dry and non-tacky feel.

The gellants themselves are preferably combinations of an ethylene/propylene/styrene copolymer and a butylene/ethylene/styrene copolymer. The ethylene/propylene and butylene/ethylene segments of these copolymers dissolve in the hydrocarbon or ester material, while the styrene portions do not. The insoluble styrene blocks naturally associate with each other via intermolecular forces and become the building blocks for a microscopic three-dimensional network with molecules of ester, occlusive oils, or other volatile oils enclosed therein.

The microscopically intertwined polymeric and ester, or oil molecules, provide a stable foundation for fine particles to be incorporated into the system and to stay suspended. For example, pigments may be incorporated into the formulation and suspended in the gel. Exemplary pigments include, but are not limited to, titanium dioxide, iron oxide, or the like. Because the fine particles are enclosed in the polymeric network, agglomeration is minimized and a stable particle suspension results. The polymers that are dissolved in the isododecane also form a continuous film when applied onto the keratin substrate. The volatile isododecane ester replaces the non-volatile oils found in conventional cosmetic foundations. The ester delivers the polymer and other suspended colorants to the substrate, then evaporates off and forms a matrix on the skin. This matrix is advantageously both water-resistant and rub-off resistant, but is nevertheless gas permeable.

Silicon-containing compounds are preferably included in the formulation and aid in forming the emulsion, improving the texture, and delivering the active ingredients of the formulation. In one preferred embodiment, a silicone-grafted copolymer may consist of a principal chain composed of an acrylic polymer and a side chain composed of dimethyl polysiloxane. Such a compound has film-forming properties similar to acrylic polymers along with the lubricity, gas permeability, water-repellency and mold-releasing properties of silicones, which enables the formation of a soft, water-repellent film that affords additional skin protection and further aids in the dispersion of the inorganic powder components of the formula.

In another preferred embodiment, silica can be included in the formulation. Silica can serve as a slip modifier, a moisture barrier, a suspending agent, and an anti-caking agent. In particular, silica dimethyl silyate can be preferably included in the formulation.

In another preferred embodiment, silicone gelling agents improve the stability of other silicone components by means of their film-forming properties, lubricity, gas permeability, water-repellency and mold-releasing properties. Silicone gelling agents additionally increase the hydrophilicty of silicones. Hydrophilic groups are preferably added by introducing polyoxyethylene chains to the polymerization mix. While silicone gelling agents containing hydrophilic groups that are cross-linked can be obtained by adding methyl hydrogen polysiloxane to the polyoxyethylene diallylether in order to gel silicone "oils," they do not allow for the incorporation of other oil-phase materials such as liquid paraffin or ester "oils." To achieve incorporation of other oil-phase materials, some of the methyl groups on the polysiloxane backbone can be preferably replaced with long alkyl chains. Another alternative to achieve incorporation of other oil-phase materials is to react the modified polysiloxane with additional polyoxyethylene diallylether. Both of these methods achieve the desired gelling of non-silicone oils and hydrophilicity of a stable water-in-silicone emulsion in the formation.

The hybrid silicone gelling agents not only gelatinize silicones and other "oils" with low viscosity but also, by absorbing large amounts of water into the gel (Nomura, T. & Yokkoji, K., Skuta, K. 1999a. *J Soc Cosmet Chem Japan* 33(2) 134-39), preferably form stable emulsions when the water phase is added to further enhance physical spreadability onto the substrate (Nomura, T. & Yokkoji, 1999b. *Material Technology* 17(8) 329-32). At the same time, the hybrid silicone gelling agents ensure suspension of pigment and other inorganic materials in the second skin matrix (Ono, I. 2001, Development of New Cosmetic Silicones for Foundation Formulations. *Cosmet & Toil* 116(3) 61-6), and deliver water-soluble active ingredients such as LYCE to the keratin substrate.

As discussed above, the gel-based formulation may include isododecane, live yeast cell extract, silicon-containing compounds, and pigment. In one preferred embodiment, the formulation includes: about 0.1-15 wt. % isododecane; about 0.15-20 wt. % LYCE; about 0.1-3 wt. % silica; and about 3-12 wt. % pigment.

In preferred embodiments, the formulation can contain a variety of preservatives, solvents, binding agents, emulsion stabilizers, film formers, anti-caking agents, moisturizers, and other ingredients commonly used in cosmetic and healing creams.

One exemplary formulation may comprise about 55-57 wt. % water, about 13-14 wt. % isododecane, about 6-7 wt. % titanium dioxide, about 4-5 wt. % cyclopentasiloxane, about 2-3 wt. % butylene glycol, about 2 wt. % dioctyldodecyl dodecaneodioate, about 2 wt. % silica dimethyl silylate, about 1-1.5 wt. % polyglyceryl-4 isostearate, about 1-1.5 wt. % cetyl dimethicone copolyol, about 1-1.5 wt. % hexyl laurate, about 1-1.5 wt. % cyclomethicone, about 1 wt. % nylon-12, about 1 wt. % sodium chloride, about 0.7 wt. % saccharomyces lysate extract, about 0.7 wt. % phenoxyethanol, about 0.6 wt. % ethylene mixed copolymer, about 0.5 wt. % PEG/PPG-20/15 dimethicone, about 0.2-0.3 wt. % quatemium-18 hectorite, about 0.25 wt. % yellow iron oxide, about 0.25 wt. % red iron oxide, about 0.25 wt. % black iron oxide, about 0.1-0.2 wt. % methicone, about 0.1-0.2 wt. % methylparaben, about 0.05-0.10 wt. % butylparaben, about 0.05-0.10 wt. % SDA alcohol 40, about 0.05 wt. % ethylparaben, and about 0.05 wt. % propylparaben. The ingredients in the formulation may be separate, or they may be pre-combined. For example, the isododecane and ethylene mixed copolymer may be added separately, or some isododecane may be pre-mixed with some or all of the copolymer. Similarly, materials such as methicone may be added to the formulation in combination with other components of the formulation, such as pigments.

In one preferred embodiment, the formulation is prepared by homogenizing a gel in a cold process. Live yeast cell extract and pigments are preferably assimilated into the gel during the homogenizing process. In one preferred embodiment, isododecane is pre-mixed in a homogenizer with ethylene/propylene/styrene copolymer and/or ethylene/butylene/styrene copolymer. In another preferred embodiment, a roller mill can be used in place of a homogenizer.

One method of preparing the exemplary formulation described above preferably involves homogenizing the base gel composition through a cold process while assimilating the LYCE and pigments. More specifically, the method involves first premixing isododecane with ethylene mixed copolymer in the main tank of a homogenizer. Then cyclopentasiloxane and PEG/PPG-20/15 dimethicone are added and the composition is mixed. Then polyglyceryl-4 isostearate, cetyl dimethicone copolyol and hexyl laurate are added, and the composition is mixed. Then cyclomethicone, quatemium-18 hectorite and SDA alcohol 40 are added, and the composition is mixed. Then dioctyldodecyl dodecaneodioate is added, and the composition is mixed. After this addition, the composition is mixed for about 15 additional minutes. In a separate vessel, nylon-12, titanium dioxide methicone, yellow iron oxide, red iron oxide, black iron oxide, and silica dimethyl silylate are pre-blended. This mixture is then added to the main tank of the homogenizer, which is set to prop mixing. The new mixture is then blended for about 45 minutes. In a separate vessel, water and saccharomyces lysate extract are blended until homogeneous. Then butylene glycol is added and the mixture is blended until homogeneous. Then phenoxyethanol, methylparaben, ethylparaben, propylparaben and butylparaben are added, and the mixture is blended until homogeneous. Then sodium chloride is added and the mixture is blended until homogeneous. Finally, this separate mixture is added to the main vessel of the homogenizer, and the whole mixture is blended for about 15 additional minutes. This exemplary method of preparation using commercially available chemical products is summarized in Table I. In an alternative preferred embodiment, a roller mill, rather than homogenization through a cold process, can be used to create the formulation.

EXAMPLES

As an example, in one embodiment, a formulation comprises 57.550 wt. % water, 13.300 wt. % isododecane, 6.860 wt. % titanium dioxide, 4.500 wt. % cyclopentasiloxane, 2.500 wt. % butylene glycol, 2.000 wt. % dioctyldodecyl dodecaneodioate, 2.000 wt. % silica dimethyl silylate, 1.365 wt. % polyglyceryl-4 isostearate, 1.365 wt. % cetyl dimethicone copolyol, 1.365 wt. % hexyl laurate, 1.155 wt. % cyclomethicone, 1.000 wt. % nylon-12, 1.000 wt. % sodium chloride, 0.700 wt. % saccharomyces lysate extract, 0.700 wt. % phenoxyethanol, 0.600 wt. % ethylene mixed copolymer, 0.500 wt. % PEG/PPG-20/15 dimethicone, 0.270 wt. % quaternium-18 hectorite, 0.245 wt. % yellow iron oxide, 0.245 wt. % red iron oxide, 0.245 wt. % black iron oxide, 0.160 wt. % methicone, 0.110 wt. % methylparaben, 0.090 wt. % butylparaben, 0.075 wt. % SDA alcohol 40, 0.050 wt. % ethylparaben, 0.050 wt. % propylparaben.

Those of ordinary skill in the art will appreciate that the element amounts listed above are exemplary only, and that the amount of any element or group of elements in the formulation can be varied within acceptable ranges that are known in the art. In addition, those of ordinary skill in the art will appreciate that other elements may be substituted for the elements listed above or that other elements may be added to the formulation. For example, in the formulation described above, the elements comprising the pigment constitute about 8 wt. % of the formulation. In other embodiments, the elements comprising the pigment may constitute a greater or lesser wt. % of the formulation. For example, in one embodiment, the elements comprising the pigment constitute about 12 wt. % of the formulation.

In another exemplary preferred embodiment, the formulation can be made as a mixture of commercially available chemical products, as summarized in Table I.

TABLE I

GEL-BASE MAKE-UP w/LYCE

| Ingredient Name | Mfr./Vendor | US INCI (EO INCI) Name | % WW |
|---|---|---|---|
| A | | | |
| FANCOL ID | Fanning/DD Chemco | Isododecane | 10.00 |
| GEL BASE 1 | Arch Personal Care | Isododecane (and) Ethylene Mixed Copolymer | 4.00 |
| SF 1528 | GE/DD Chemco | Cyclopentasiloxane (and) PEG/PPG-20/15 Dimethicone | 5.00 |
| A_L WE-09 | Goldschmidt/Ross Org | Polyglycervl-4 Isostearate (and) Cetyl Dimethicone (Copolyel) (and) Hexyl Laurate | 4.00 |
| BENTONE GEL VS-5 | Elementis | Cyclomethicone (and) Quaternium-18 Hectorite (and) SDA Alcohol 40 | 1.50 |
| LIQUIWAX DIADD | Arch Personal Care | Diocetyldodecyl Dodecaneodiate | 2.00 |
| B | | | |
| ORGASOL 2002 EX DN AT | Lipo/DD Chemco | Nylon-12 | 1.00 |
| TIO-SI | Cardre | Titanium Dioxide (and) Methicone | 7.00 |
| YELLOW IRON OXIDE S12 | Cardre | Iron Oxide (and) Methicone | 0.25 |
| RED IRON OXIDE S12 | Cardre | Iron Oxide (and) Methicone | 0.25 |
| BLACK IRON OXIDE S12 | Cadre | Iron Oxide (and) Methicone | 0.25 |
| WACKER HDK H20 | Wacker-Chemic | Silca Dimethyl Silylate | 2.00 |
| C | | | |
| DI WATER | | Water (Aqua) | 55.45 |
| BIODYNES TRF 25% Soln. | Arch Personal Care | Water (and) Saccharomyces Lysate Extract | 2.80 |
| BUTYLENE GLYCOL USP | Ashland | Butylene Glycol | 2.50 |

TABLE I-continued

GEL-BASE MAKE-UP w/LYCE

| Ingredient Name | Mfr./Vendor | US INCI (EO INCI) Name | % WW |
|---|---|---|---|
| ONIPHEN P-23 | Lipo/DD Chemco | Phenoxyethanol (and) Methylparaben (and) Ethylparaben (and) Propylparben (and) Butylparaben | 1.00 |
| CANNERS 999 | Open | Sodium Chloride | 1.00 |
| | | TOTAL | 100.00 |

PROCEDURE
1-Using a homogenizer in the main tank, pre-mix FANCOL ID and GEL BASE 1 until smooth.
2-When homogeneous, add remaining "A" ingredients in order indicated, mixing well between each addition, and continue to mix for 15 minutes.
3-In a separate vessel, pre-blend "B" ingredients.
4-When well blended, switch main tank agitation to prop mixing, add pre-blend to batch, and continue to mix for 45 minutes.
5-In a separate vessel, pre-blend "C" ingredients in order indicated, mixing well between each addition until homogeneous.
6-When homogeneous, add "C" pre-blend to batch, and continue to mix for at least 15 minutes.
Specifications pH: N/A
Viscosity: >20,000 cps Those of ordinary skill in the art will appreciate that the commercially available ingredients listed above are exemplary only, and that the elements in the formulation may be obtained using ingredients other than those listed above. In addition, those of ordinary skill in the art will appreciate that the amount of any ingredient or group of ingredients listed above can be varied depending on the desired concentration of elements in the formulation.

This gel-based formulation allows the skin to appear undamaged while simultaneously delivering the LYCE biofactors to repair skin. The wound healing factor enhances skin repair by facilitating oxygen utilization of fibroblasts and metabolic activity, which helps lead to greater and more rapid collagen and elastin production. The formulation is designed to spread smoothly, to deliver color, maintain gas permeability, and stimulate oxygen consumption at wounds.

The gel-based formulation and methods according to the present invention have been disclosed in detail in connection with the preferred embodiments, but these embodiments are disclosed by way of examples only and are not to limit the scope of the present invention, which is defined by the claims that follow. One of ordinary skill in the art will appreciate many variations and modifications within the scope of this invention.

What is claimed is:

1. A gel-based formulation for topical application comprising:

live yeast cell extract comprising about 0.15% to about 20% by weight of said gel-based formulation;

isododecane comprising about 0.1% to about 15% by weight of said gel-based formulation;

silica dimethyl silylate; and one or more metal-based pigments chosen from the group consisting of titanium dioxide, yellow iron oxide, red iron oxide, and black iron oxide.

2. The gel-based formulation of claim 1, wherein the live yeast cell extract and the pigment are suspended in the gel.

3. The gel-based formulation of claim 1, wherein the gel comprises:

ethylene/propylene/styrene copolymer; and/or ethylene/butylene/styrene copolymer.

4. A method of simultaneously healing and disguising wounds on human skin, comprising topically applying the gel-based formulation of claim 1 to the skin.

5. The gel-based formulation of claim 1, wherein the live yeast cell extract comprises about 0.5% to about 2% by weight of said gel-based formulation.

6. The gel-based formulation of claim 1, wherein the silica dimethyl silylate comprises about 1.5% to about 2% by weight of said gel-based formulation.

* * * * *